United States Patent [19]
Fraschini et al.

[11] Patent Number: 5,272,141
[45] Date of Patent: Dec. 21, 1993

[54] CONTRACEPTIVE AND MENSTRUAL CYCLE CONTROLLING DRUG HAVING ONCOSTATIC THERAPEUTIC PROPERTIES FOR TREATMENT OF MAMMARY TUMORS AND MELANOMAS, AND METHOD THEREFOR

[76] Inventors: Franco Fraschini; Bojidar Stankov; Luigi Di Bella; Ermanno Duranti; Aldo Lagguzzi, all of Via Prandina, 7, 20127 Milano, Italy

[21] Appl. No.: 767,084

[22] Filed: Sep. 27, 1991

[30] Foreign Application Priority Data

Sep. 28, 1990 [IT] Italy ................. 21596 A/90
Dec. 11, 1990 [IT] Italy ................. 22338 A/90
Sep. 16, 1991 [IT] Italy ............. MI91A-02438

[51] Int. Cl.$^5$ .................... A61K 31/56; A61K 31/405
[52] U.S. Cl. .................... 514/178; 514/181; 514/415; 514/843
[58] Field of Search ............. 514/178, 181, 415, 843

[56] References Cited

U.S. PATENT DOCUMENTS 4,855,305 8/1989 Cohen .................. 514/171

Primary Examiner—Frederick E. Waddell
Assistant Examiner—Kimberly R. Jordan
Attorney, Agent, or Firm—Bucknam and Archer

[57] ABSTRACT

The present invention relates to a drug for human use, having contraceptive and menstrual cycle controlling properties, characterized in that the drug comprises N-acetyl-5-methoxytryptamine or melatonin, in a dose of 100-200 mg per day, N-acetyl-2-bromo-5-methoxytryptamine or 2-bromomelatonin in a dose of 25-50 mg per day, N-acetyl-2-iodo-5-methoxytryptamine or 2-iodomelatonin, in a dose of 20-40 mgs per day, in association with a progestine compound. The administration is carried out for 23 days, by using an association of 2-iodomelatonin and/or melatonin and/or 2-bromomelatonin and a progestinic compound, followed by 5 days in which only 2-iodomelatonin and/or melatonin and/or 2-bromomelatonin is administered; the drug having oncostatic preventive and therapeutic properties, in mammary tumours and melanomas, characterized by the use of 2-iodomelatonin, melatonin and 2-bromomelatonin respectively with doses of 20-40 mgs., 100-200 mgs., 25-50 mg per day; and the drug having moreover antikinetosic properties, and being characterized by the use of 2-iodomelatonin in a dose per day of 2.5 mg.; melatonin, in a dose per day of 10 mg and 2-bromomelatonin in a dose per day of 3.5 mg, either individually and/or in association with the acetyl coenzyme A-(AcCoA), in a dose of 8-10 mg per day.

11 Claims, No Drawings

CONTRACEPTIVE AND MENSTRUAL CYCLE CONTROLLING DRUG HAVING ONCOSTATIC THERAPEUTIC PROPERTIES FOR TREATMENT OF MAMMARY TUMORS AND MELANOMAS, AND METHOD THEREFOR

BACKGROUND OF THE INVENTION

The present invention relates to a contraceptive and menstrual cycle controlling drug having oncostatic, antikinetosic preventive and therapeutic properties for treating mammary tumors and melanomas and a method therefor.

After several years of studies and experiments, related to the mechanism of action of melatonin, this indole is at present considered as the most important hormonal product of the pineal gland.

The developments in the field of receptor research have led to the localization of two important receptor sites of melatonin in SNC: the median eminence, pars tuberalis of the pituitary gland, and the supra chiasmatic nuclei of the hypothalamus.

Intensive studies have shown the biological basis for the mechanism of action of melatonin and its two halogen-derivatives (2-bromo and 2-iodomelatonin).

Experiments carried out by several researcher groups have confirmed some of the previous discoveries, and have shown that the ability of melatonin to inhibit reproduction, under given experimental conditions, can be related to a direct action of the indole on the hormone responsive elements in the SNC and the pituitary gland.

Thus, from prior research it has been known that melatonin can potentially be used as human contraceptive drug.

In fact, recently performed research has shown the possibility of using melatonin in association with a progestin compound (norethisterone), as a powerful contraceptive, which, moreover, provides several advantages such as: a low conception risk (less than 1%), lower risk of vascular disturbances (no estrogenic compounds are used) and less painful premenstrual and menstrual periods as well as a less painful premenopause period (melatonin and agonists thereof are known to have sedative effects).

Norethisterone alone, as well as other progestin derivatives, have been used as contraceptives in the recent years, and they are generally known under the name "mini-pill".

Norethisterone, when used as a "mini-pill", however has not provided remarkable results in preventing undesired pregnancies (about 2.35%).

Other progestinic compounds, such as 1-norgestrel, have been found to provide better results, with reduced doses (0.08–0.16 mg).

On the other hand, it has been found that melatonin, in order to express its contraceptive action. required comparatively high doses (100–200 mg).

SUMMARY OF THE INVENTION

The main object of the present invention is to provide a drug which, the drug efficiency being the same, allows the doses to be drastically reduced.

Another object of the present invention is that to improve the activity of melatonin, so as to reduce, under like indication and safety conditions, the dose levels thereof.

According to one aspect of the present invention, the above mentioned objects, as well as yet other objects, which will become apparent hereinafter, are achieved by a drug for human use, having contraceptive and menstrual cycle controlling properties, characterized in that the said drug comprises 2-iodomelatonin or 2-bromomelatonin, respectively with a dose of 20–40 mg and 25–50 mg, in association with a progestin substance.

According to the invention, in order to improve the activity of melatonin and reduce the dose thereof, halogenated derivatives are used, which render agonists with extremely improved qualities in respect to melatonin.

In particular, 2-iodomelatonin and 2-bromomelatonin have been used, which have been found to be biologically more active, both in vivo and in vitro, and, more specifically, having an activity of about seven to ten times higher than that of melatonin.

Moreover, the use of 2-iodomelatonin and/or 2-bromomelatonin allows to use at a whole a lower amount of the progestinic compound in the combinations.

Additionally, the possibility of side effects is further reduced, while providing the above disclosed results.

It has been clearly demonstrated that by suspending the long term treatment with melatonin or 2-iodomelatonin or 2-bromomelatonin in association with progestagens (norethisterone, 1-norgerstrel, norgestrel, and other), used as contraceptive and menstrual cycle controlling compounds, the fertility of the treated women recovered to normal levels.

With respect to the clinic experimentation, preliminary tests has been carried out on eighty two female patients, having an age between 18 and 46 years, with the following associations of the disclosed substances:

a) melatonin and norethisterone with doses per day of respectively 100–200 mg and 0.30–0.50 mg:

b) melatonin and 1-norgestrel with doses per day of respectively 100–200 mg and 0.08–0.16 mg;

c) 2-iodomelationin and norethisterone with doses per day of respectively 20–40 mg and 0.30–0.50 mg; mg;

d) 2-iodomelatonin and norgestrel with doses per day of respectively 20–40 mg and 0.35–0.80 mg;

e) 2-iodomelatonin and 1-norgestrel with doses per day of respectively 20–40 mg and 0.08–0.16 mg;

f) 2-bromomelatonin and norethisterone with doses per day of respectively 25–50 mg and 0.30–0.50 mg;

g) 2-bromomelatonin and norgestrel with doses per day of respectively 20–40 mg and 0.35–0.80.

h) 2-bomromelatonin and 1-norgestrel with doses pro die of respectively 20–40 mg and 0.08–0.16 mg.

The use has been mainly made with a contraceptive purpose.

After four months of treatment no pregnancy has been recorded, with the exception of a patient at the age of 34, who arbitrarily interrupted for 12 days the administration of the association melatonin-norethisterone.

Accordingly, it should be pointed out that the association of 2-iodomelatonin and 2-bromomelatonin with progestin derivatives (such as norethisterone. 1-norgestrel, norgestrel and other) has shown a contraceptive activity in about 99% of the cases, and that this association allows to use the progestin compounds in lower amounts, in respect to the amounts required when they are used in other combinations.

Moreover, it should be pointed out that by avoiding the use of estrogens, the risk of all side effects, such as vascular problems and steroid dependent neoplasias, is greatly reduced.

Moreover, 2-iodomelatonin and 2-bromomelatonin can be used in doses five to ten times lower than those of melatonin.

Additionally, the menstrual bleeding period and that preceding the latter are reported less painful, and the recovery of the fertility is obtained by interrupting the administration of associations herein considered.

It should be pointed out that the optimal approach is to administer the drug for 23 days, i.e. the association 2-iodomelatonin or melatonin or 2-bromomelato- nin with one of the progestinic derivatives thereof and, for the following five days, the 2-iodomelatonin or melatonin or 2-bromomelatonin alone.

While a possible relationship between the pineal gland (melatonin) and tumour growth and spread has been previously hypothesized, the mode and site of action of this indole and its derivatives are at present still subject of extensive studies.

The peripheral blood plasma levels of melatonin were reported altered in patients affected by several neoplasms, and the urinary excretion of the metabolites thereof has been found to be lower in similar types neoplasms.

Hyperplasia of the pineal gland, which could also indicate an alteration in the production of melatonin, has been observed in patients deceased because of different types of neoplastic diseases.

Powerful oncostatic effects of 2-iodomelatonin and 2-bromomelatonin have been observed in "vitro" and in "vivo".

In "vitro", the treatment of several human neoplastic cell lines with 2-iodomelatonin and 2-bromomelatonin has caused dose-dependant inhibition of the growth (ovarian cell lines SK-OV-3 and JA, the bladder carcinoma RT-112 and the mammary carcinoma MCF-7 cells).

In our studies and experiments we have obtained an inhibition greater than 75% of the growth in primary cultures of metastatic nodules of a human malignant melanoma upon treatment in "vitro" with 2-iodomelatonin and 2-bromomelatonin and in primary cultures from different human melanomas, a growth inhibition has been obtained in 6 of 11 patients studied.

2-iodomelatonin and 2-bromomelatonin have also inhibited the growth of the cellular lines MCF-7 in a dose dependant manner, and melatonin has temporarily caused an increase of the estrogen receptor number.

The possible influence of 2-iodomelatonin and 2-bromomelatonin on the expression of receptors for other hormones or growth factors has not been clarified yet.

Some human malignant melanomas express estrogen receptors and their presence seem to be related to a favourable prognosis.

The effect of the treatment with 2-iodomelatonin and 2-bromomelatonin in "vivo" and in "vitro" on the expression of the estrogen receptors in malignant melanomas is still subject of extensive studies.

The results obtained in our laboratories, however, have demonstered that 2-iodomelatonin and 2-bromomelatonin cause a reduction both in the number of the lung metastasis and of the local growth of tumors in mice inplanted with B-16 melanoma or MS-2 fibrosarcoma cells.

This data suggest that the inhibition of the neoplastic cellular proliferation by 2-iodomelatonin and 2-bromomelatonin may be due to the binding to a specific receptor.

Recently, the expression of a specific and saturable binding of 2-(125I)-iodomelatonin has been demonstrated and confirmed in cell cultures, neoplasms and hyperplasias from both humans and laboratory animals.

The experimental tests however have shown that while in normal tissues, the binding of 2-iodomelatonin, 2-bromomelatonin an melatonin is of a high affinity, saturable and specific, in neoplastic tissues, the binding affinity is much lower.

The long term treatment with melatonin, 2-bromomelatonin and 2-iodomelatonin has contraceptive and menstrual cycle adjusting substances and as demonstrated in the human arrest and partial regression of tumors, have been observed in some cases, this showing that the three indole derivatives can act as oncostatic agents, in concert with the standard chemotherapy.

More recent data have shown that 2-iodomelatonin and 2-bromomelatonin bind to the cellular membranes of some neoplasms such as melanoma, mammary gland cancer, as well as cellular lines infected with oncogenic viruses.

2-iodomelatonin and 2-bromomelatonin appear to act both during the progression of the tumor, and during the starting phase, and may act by suppressing the mitogenic effect of estradiol in estrogen-dependent tumours.

The hematic, biochemical and electrophoretic tests, as well as the tests of status and weight of the organs, bone marrow and the hystological tests have not shown any particularly toxicity, following treatments with melatonin, 2I or 2B.

With respect to the antikinetosic action, it is appropriate to make some preliminary remarks about the action provided by the indole derivatives, related to neurovegetative problems such as those associated with travels by car, sea and air: two are the important things to be considered:

1) the cervical musculature:
2) the organs involved directly with equilibrium, such as the semicircular canals, the utricle, the pathways deriving from retina.

The light, depending on the way by which it hits the retina, affects the adjusting of the muscular tone of the eye muscles.

The tension of these muscles is transmitted to other substrates which act on the cervical muscle tone and on the muscle tone of the whole body.

Accordingly, we have 3-4 feed-back phenomena, and because the conduction rate in all of these pathways is in the order of 60 m/ms, it is understood that overall event occurs in a very short time.

The object is clearly seen when the muscle tone will be already self-adjusted, based on the distance and size, with respect to the structure of the considered object.

Melatonin action at the level of the retina has been clearly established. Both, 2-iodomelatonin and 2-bromomelatonin were found to be potent inhibitors of stimulated dopamine release in this organ, very much like melatonin, and are thought to participate in the control of disk shedding and other local adaptive events, related to the speed of perception.

On the other hand, sites of action of melatonin distant from those in the retina may be involved, such as those found in the different parts of the visual pathways and the limbic system.

In the case of a pineal insufficiency with respect to the synthesis of melatonin, it would be suitable to associate with melatonin, 2-bromomelatonin, 2-idomelatonin, substances adapted to stimulate the endogenous biosynthesis of melatonin such as Acetilloenzima A, "reuptake" inhibitors of norepinephrine.

Accordingly, the association melatonin or 2-bromomelatonin or 2-iodomelatonin with acetyl CoA not only acts to stimulate the production of melatonin, but also allow for a better performance of the rest neuro-endocrine structures.

The present invention also relates to methods for the synthesis of 2-bromo and 2-iodomelatonine, which method is carried out based on the following functional diagrams:

SYNTHESYS OF 2-BROMOMELATONIN (N-acetyl-2-bromo-5-methoxytriptamine)

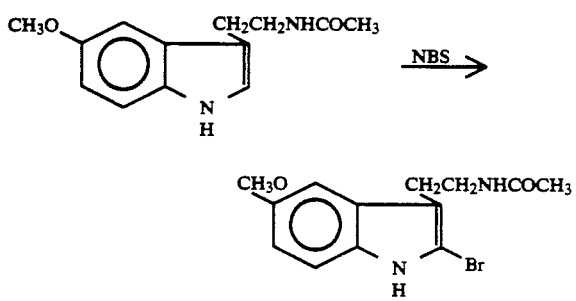

To a solution of melatonin (1.16 g 5 mM) in anhydrous acetic acid (10 ml) there is slowly added, under stirring, a solution of bromosuccinimide (NBS: 0.89 g; 5 mM), in anhydrous acetic acid (30 ml).

The reaction mixture is stirred under a stream of nitrogen at room temperature for three hours. At the end it is cooled in an ice bath and neutralized to a pH 7 by a solution of 50% NaOH, still under nitrogen; a cream suspension is thereby obtained.

The aqueous phase is extracted four times with chloroform: the combined organic phases are washed two times with a saturated solution of NaCl and dried on anhydrous sodium sulphate. The solvent is removed under reduced pressure, so as to provide 2 g of a raw product in the form of a brown-yellow oil.

The raw product is purified by flash chromatography (silica gel 80:1; E-tOAc-cyclohexane 8:2) thereby providing 0.70 g (45% yield) of product.

It is crystallized from EtOAc-hexane: mp: 146°-149° C. (on Kofler).

The reaction can be followed by TLC, by using ethyl acetate as mobile phase.

The NMR spectrum confirms che structure of the obtained product.

SYNTHESIS OF 2-IODOMELATONIN (N-acetyl-2-iodo-5-methoxytriptamine)

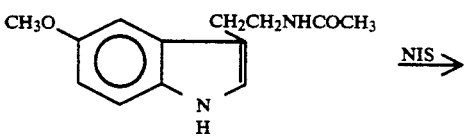

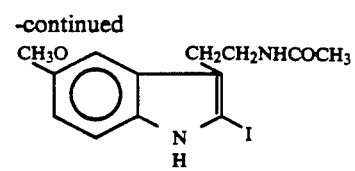

To a solution of melatonin (2.32 g: 10 mM) in chloroform (70 ml) cooled at −20° C. there is added N-iodosuccinimide (NIS:2.25 g; 10 nM); the reaction mixture is stirred at −20° C. for 4.5 hours.

The organic solution is washed with a 2N sodium carbonate solution (1 time) and with water (two times) and then it is dried on anhydrous sodium sulfate.

The solvent is removed under reduced pressure and the raw material is purified by flash chromatography (anhydrous alumina 40:1; EtOAc) thereby providing 0.5 g of a product which is recrystalized from EtOAc with traces of hexane.

There are 0.4 g obtained (yield 10–12%) of a product having a m.p. =142° C.

The NMR spectrum confirms the structure of the obtained product.

TOXICITY

In the specific case of melatonin, acute

| | | |
|---|---|---|
| 1) | Rats, intraperitoneally | DL50 = 462 mg · Kg |
| 2) | Rats, per os | DL50 = greater than 800 mg/Kg |
| 3) | rabbits, intravenously (observation period 14 days) and the sub-acute toxicity in: | DL50 = 394 mg/Kg |
| 4) | rats subcutaneously (observation period 25 days). | DL50 = greater than 192 mg/Kg | the symbol DL50 means the amount of material which kills 50% of the animals tested The haematochemical, electrophoretic tests, and the tests for determining the status and weight of organs, bone marrow, and the hystological tests have not shown any particular toxicity and, based on these observations, which show the low toxicity of the individual compounds and associations, a favourable opinion has been released about the starting of the clinical experimentation.

With respect to the toxicity of 2-iodomelatonin and 2-bromomelatonin, the acute toxicity tests have been carried out:

1) in rats per os: DL50 greater than 200 mg/Kg 2) in mice per os and intraperitoneally: DL50 greater than 100 mg/Kg.

The invention as disclosed is susceptible to several modifications and variations all of which will come within the spirit and scope of the appended claims.

Moreover, all of the details related to the ration, as well as the illustrated doses can be changed depending on the specific patients to be treated, without departing from the scope of the invention which is mainly based on the use of melatonin, 2-iodomelatonin and 2-bromomelatonin and derivatives thereof, either individually and/or in association with one another, in the contraceptive therapy and in the menstrual cycle adjusting therapy, as well as in the oncostatic preventive therapy of mammary tumors and melanoma, and in the antikinetosic therapy.

We claim:

1. A composition for affecting the menstrual cycle and effecting contraception in a female, for exerting an oncostatic effect in mammary carcinoma and malignant melanoma, consists of the active ingredients 2-iodomelatonin in the amount of 20–40 mgs and a progestagen in the amount of 0.08–0.80 mgs.

2. The composition according to claim 1 wherein said progestagen is norethisterone in the amount of 0.3–0.5 mgs.

3. The composition according to claim 1, wherein said progestagen is l-norgestrel in the amount of 0.35–0.80 mgs.

4. The composition according to claim 1, wherein said progestagen is norgestrel in the amount of 0.08–0.16 mgs.

5. A composition for affecting the menstrual cycle and effecting contraception in a female, for exerting an oncostatic effect in mammary carcinoma and malignant melanoma, which consists of the active ingredients 2-bromomelatonin in the amount of 25–50 mgs and a progestagen in the amount of 0.08–0.80 mgs.

6. The composition according to claim 5, wherein said progestagen is norethisterone in the amount of 0.3–0.5 mgs.

7. The composition according to claim 5, wherein said progestagen is l-norgestrel in the amount of 0.08–0.16 mgs.

8. The composition according to claim 5, wherein said progestagen is norgestrel in the amount of 0.35–0.8 mgs.

9. The method of affecting the menstrual cycle and inducing contraception in a woman which consists of administering to said woman a composition consisting of the active ingredients;
   a) 20–40 mgs of 2-iodomelatonin and b) 0.3–0.5 mgs of norethisterone, or 0.35–0.80 mgs of norgestrel or 0.08–0.16 mgs of l-norgestrel per day for a period of 23 days, followed by administration of 2-iodomelatonin for 5 days.

10. The method of affecting the menstrual cycle and inducing contraception in a woman which consists of administering to said woman a composition consisting of the active ingredients;
   a) 20–50 mgs of 2-bromomelatonin and b) 0.3–0.5 mgs of norethisterone, or 0.35–0.80 mgs norgestrel or 0.08–0.16 mgs of l-norgestrel per day for a period of 23 days, followed by administration of 2-bromomelatonin for 5 days.

11. The method of inhibiting breast cancer and malignant carcinoma in a patient which consists of administering to said patient in need of treatment an effective dose of 2-iodomelatonin or 2-bromomelatonin.

* * * * *